(12) United States Patent  
Houck

(10) Patent No.: US 11,137,331 B2  
(45) Date of Patent: Oct. 5, 2021

(54) MULTISPECTRAL SENSOR BASED ALERT CONDITION DETECTOR

(71) Applicant: VIAVI Solutions Inc., San Jose, CA (US)

(72) Inventor: William D. Houck, Santa Rosa, CA (US)

(73) Assignee: VIAVI Solutions Inc., San Jose, CA (US)

(*) Notice: Subject to any disclaimer, the term of this patent is extended or adjusted under 35 U.S.C. 154(b) by 0 days.

(21) Appl. No.: 16/530,524

(22) Filed: Aug. 2, 2019

(65) Prior Publication Data

US 2020/0064248 A1 Feb. 27, 2020

Related U.S. Application Data

(60) Provisional application No. 62/720,455, filed on Aug. 21, 2018.

(51) Int. Cl.

| | |
|---|---|
| *G01N 15/02* | (2006.01) |
| *G01N 21/53* | (2006.01) |
| *G01N 33/00* | (2006.01) |
| *G01J 3/44* | (2006.01) |
| *G08B 17/107* | (2006.01) |

(52) U.S. Cl.
CPC ........ *G01N 15/0211* (2013.01); *G01J 3/4412* (2013.01); *G01N 21/53* (2013.01); *G01N 33/0063* (2013.01); *G08B 17/107* (2013.01)

(58) Field of Classification Search
CPC .............. G01N 15/06; G01N 15/0205; G01N 15/0211; G01N 33/0063; G01N 2015/0693; G01N 2015/0046; G01N 21/53; G01J 3/4412; G01J 3/513; G08B 17/103; G08B 17/107; G08B 17/117

See application file for complete search history.

(56) References Cited

U.S. PATENT DOCUMENTS

| | | |
|---|---|---|
| 3,982,130 A | 9/1976 | Trumble |
| 5,798,701 A * | 8/1998 | Bernal ................... G08B 17/10 |
| | | 250/574 |

(Continued)

FOREIGN PATENT DOCUMENTS

| | | |
|---|---|---|
| DE | 102007021677 A1 | 11/2008 |
| EP | 2053575 A1 | 4/2009 |
| EP | 3082117 A1 | 10/2016 |

OTHER PUBLICATIONS

Partial European Search Report for Application No. EP19191915.8, dated Nov. 25, 2019, 18 pages.

(Continued)

*Primary Examiner* — Sang H Nguyen  
(74) *Attorney, Agent, or Firm* — Harrity & Harrity, LLP

(57) ABSTRACT

An optical detector device may receive a spectroscopic measurement from a multispectral sensor. The optical detector device may determine, based on the spectroscopic measurement, a particulate size of a particulate. The optical detector device may determine, based on the spectroscopic measurement, an identification of the particulate. The optical detector device may determine, based on the particulate size and the identification of the particulate, that an alert condition is satisfied. The optical detector device may trigger an alert based on determining that the alert condition is satisfied.

20 Claims, 9 Drawing Sheets

(56) References Cited

U.S. PATENT DOCUMENTS

| | | | | |
|---|---|---|---|---|
| 6,011,478 | A | 1/2000 | Suzuki et al. | |
| 2002/0084907 | A1* | 7/2002 | Rattman | G08B 29/183 340/630 |
| 2002/0142477 | A1* | 10/2002 | Lewis | G01N 33/0031 436/151 |
| 2005/0110633 | A1* | 5/2005 | Lovell | G08B 29/183 340/522 |
| 2007/0164220 | A1* | 7/2007 | Luk | G01N 21/3504 250/338.5 |
| 2008/0297360 | A1* | 12/2008 | Knox | G08B 29/185 340/628 |
| 2009/0184830 | A1* | 7/2009 | Watabe | G08B 17/113 340/628 |
| 2012/0126975 | A1* | 5/2012 | Gonzales | G08B 29/26 340/540 |
| 2012/0285710 | A1* | 11/2012 | Umehara | A62C 37/36 169/61 |
| 2015/0213697 | A1* | 7/2015 | Knox | G08B 17/10 382/103 |
| 2015/0339896 | A1* | 11/2015 | Stagg | G08B 17/10 340/521 |
| 2016/0042638 | A1* | 2/2016 | Sangha | G08B 29/26 340/628 |
| 2017/0184496 | A1 | 6/2017 | Knox et al. | |

OTHER PUBLICATIONS

Chamberlin et al., "Physics of Particle Size Spectrophotometry", 8 pages.

* cited by examiner

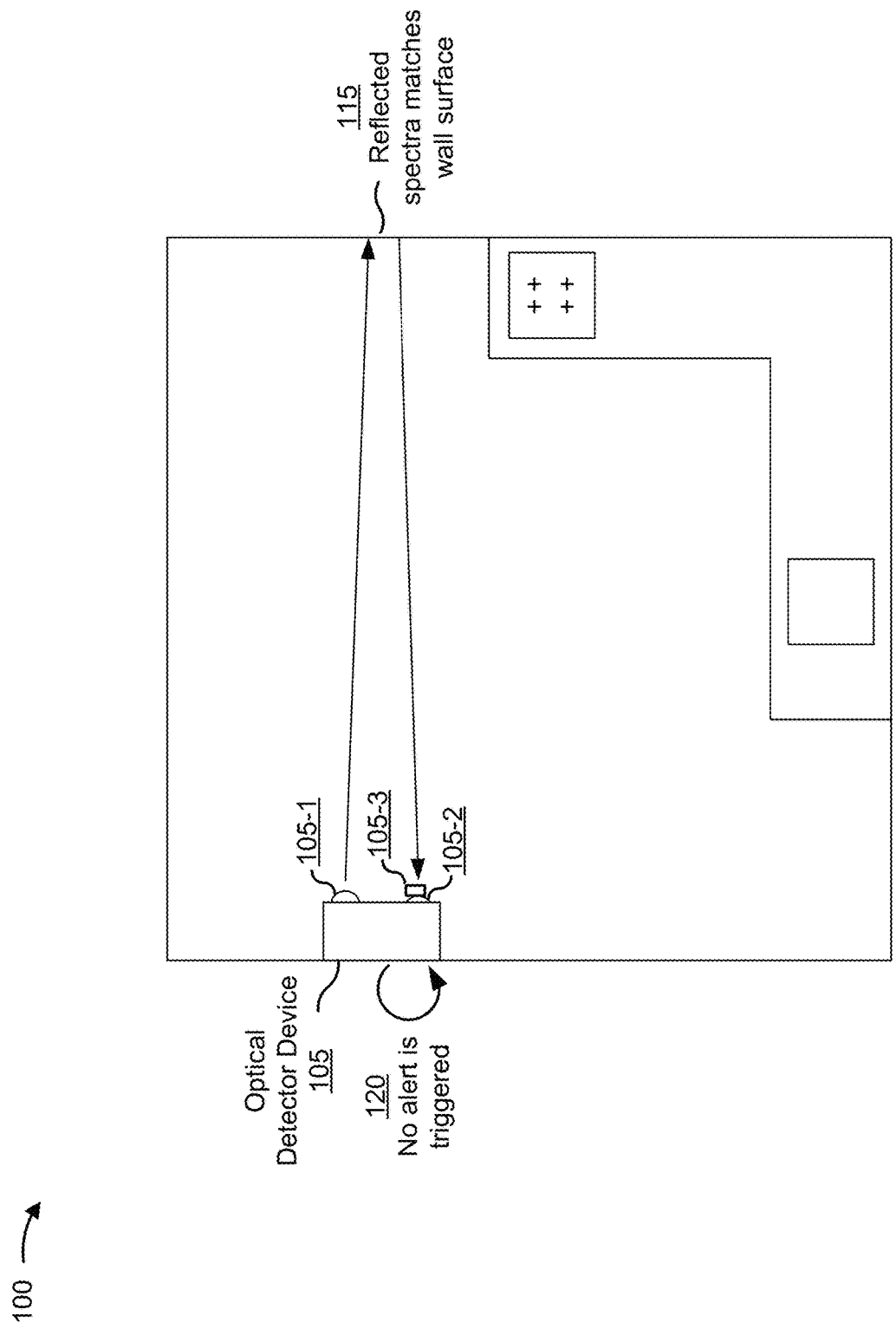

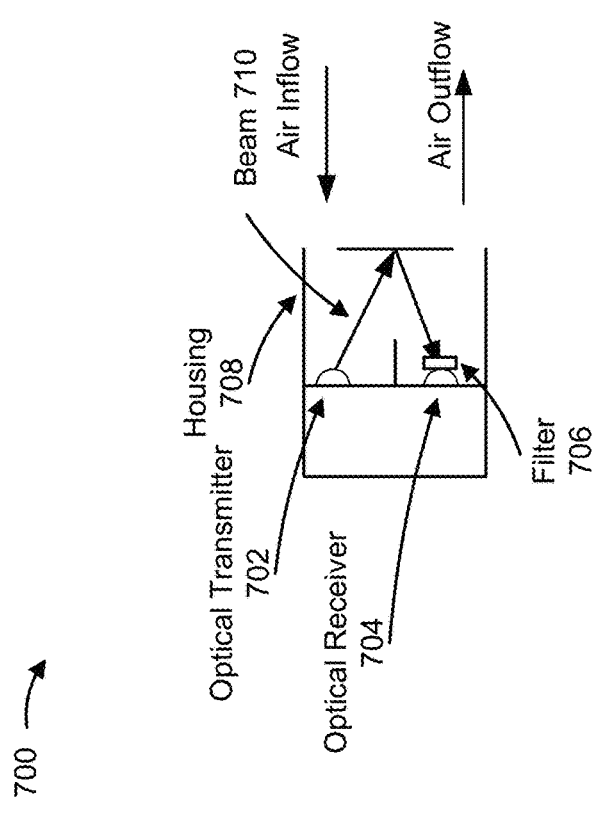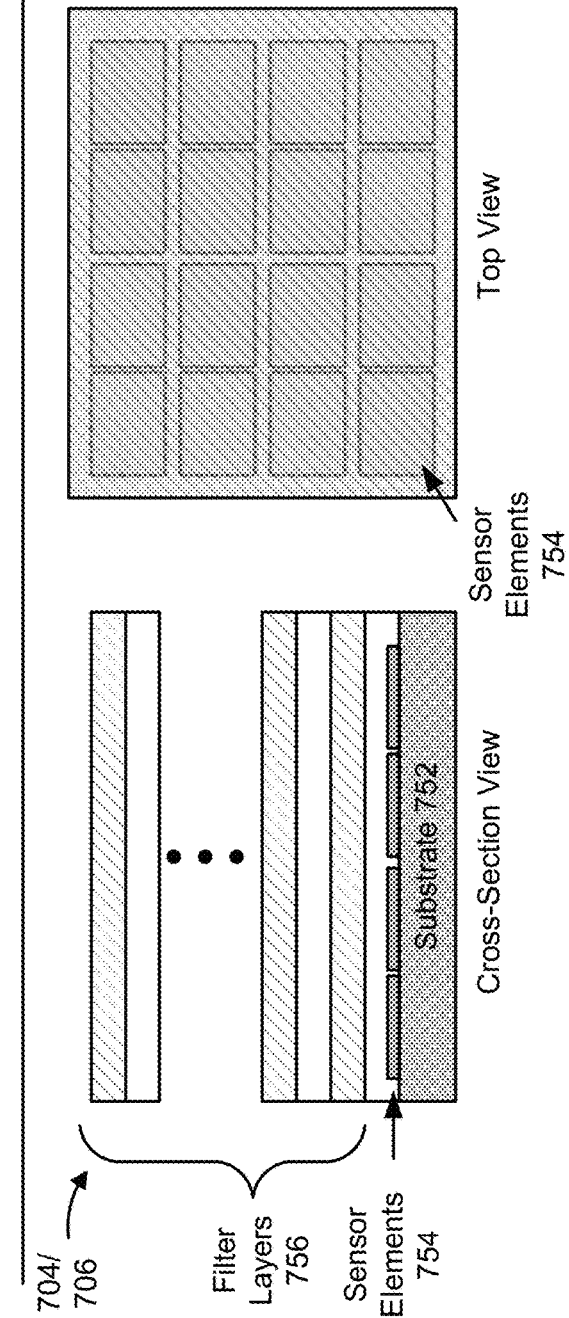

MULTISPECTRAL SENSOR BASED ALERT CONDITION DETECTOR

RELATED APPLICATION(S)

This application claims priority under 35 U.S.C. § 119 to U.S. Provisional Patent Application No. 62/720,455, filed on Aug. 21, 2018, and entitled "SPECTROSCOPIC DETECTOR FOR OPTICAL PARTICLE SIZING AND DETECTION," the content of which is incorporated by reference herein in its entirety.

BACKGROUND

Fire detectors may be used in households to detect a presence of a fire. For example, an ionization fire detector may use a radioisotope to ionize air. In this case, the ionization fire detector may detect a differential between an electric current flow in ionized air in a sealed chamber without smoke present and an electric current flow in ionized air in an open chamber with smoke present. Based on the differential exceeding a threshold amount, the ionization fire detector may provide an alert.

An optical fire detector may project a beam of light and may measure a received intensity of the light to distinguish between air without smoke (e.g., which does not reflect or scatter the light) and air with smoke (e.g., which does reflect and scatter the light). Based on the received intensity exceeding a threshold amount, the optical fire detector may provide an alert. A carbon dioxide fire detector may detect a level of carbon dioxide ambient in air and determine that the level of carbon dioxide exceeds a threshold indicative of a fire within a proximity of the carbon dioxide fire detector.

SUMMARY

According to some implementations, an optical detector device may include one or more memories; and one or more processors, communicatively coupled to the one or more memories, configured to receive a spectroscopic measurement from a multispectral sensor; determine, based on the spectroscopic measurement, a particulate size of a particulate; determine, based on the spectroscopic measurement, an identification of the particulate; determine, based on the particulate size and the identification of the particulate, that an alert condition is satisfied; and trigger an alert based on determining that the alert condition is satisfied.

According to some implementations, a fixed angle multispectral sensor device may include an optical transmitter to transmit a beam with a range of wavelengths; a multispectral filter or lens to direct a reflection of the beam into a plurality of channels; an optical receiver including a sensor element array to receive the reflection of the beam via the plurality of channels and to perform a spectroscopic measurement; and one or more processors to determine that an alert condition is satisfied based on the spectroscopic measurement and trigger a response action based on determining that the alert condition is satisfied.

According to some implementations, a method may include transmitting, by a multispectral sensor device, a beam toward a volume for spectroscopic measurement; receiving, by the multispectral sensor device, a reflection of the beam based on transmitting the beam toward the volume for spectroscopic measurement; determining, by the multispectral sensor device, a spectroscopic measurement of particulate matter in the volume for spectroscopic measurement; classifying, by the multispectral sensor device, the spectroscopic measurement into a particular classification using a spectroscopic classification model; determining, by the multispectral sensor device, that the spectroscopic measurement indicates that an alert condition is satisfied, based on classifying the spectroscopic measurement into the particular classification; and performing, by the multispectral sensor device, an alert action to indicate the alert condition.

BRIEF DESCRIPTION OF THE DRAWINGS

FIGS. 1A-1C are diagrams of an example implementation described herein.

FIGS. 7A and 7B are diagrams of an example implementation described herein.

DETAILED DESCRIPTION

Figure 1B:
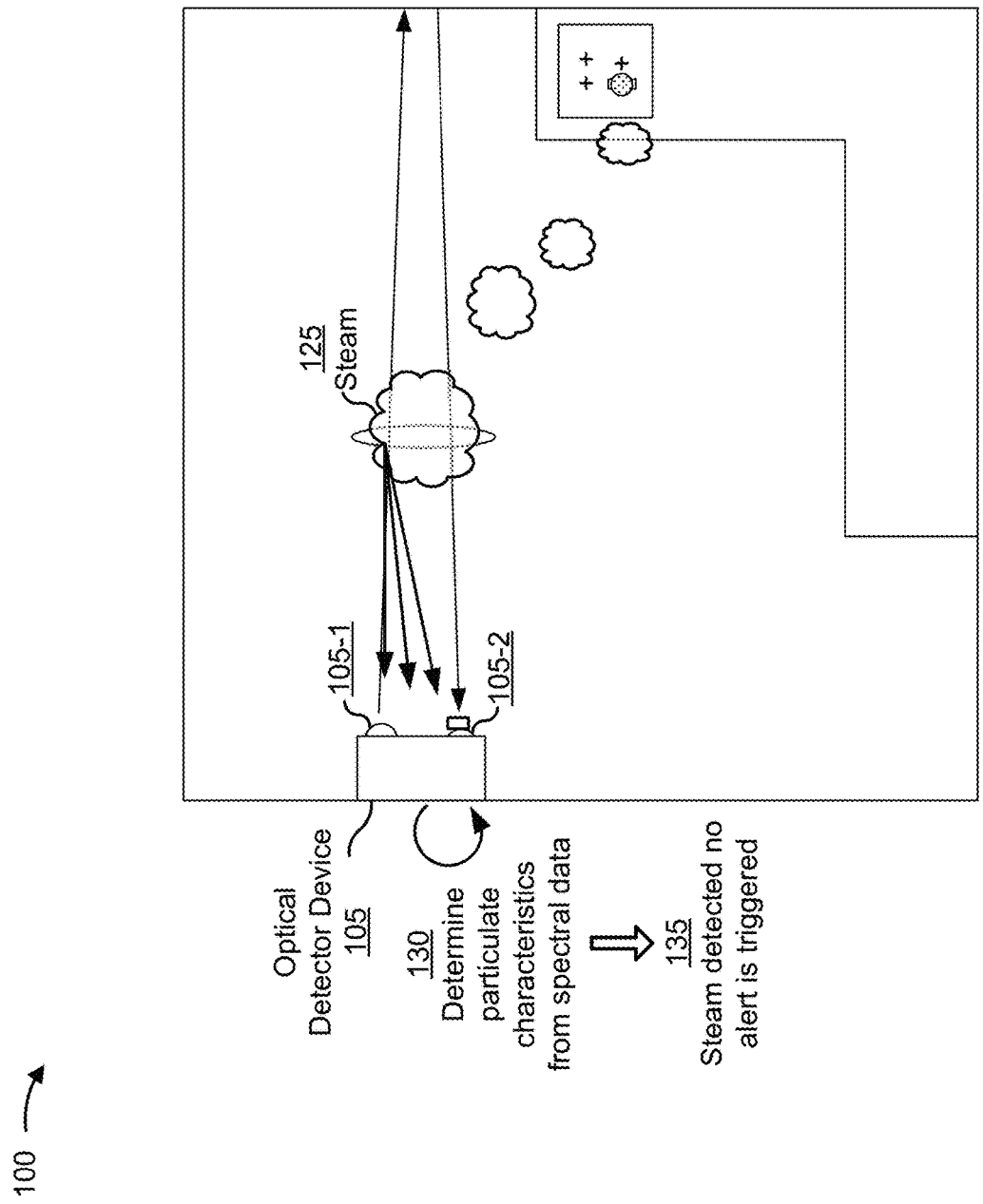

The following detailed description of example implementations refers to the accompanying drawings. The same reference numbers in different drawings may identify the same or similar elements.

A home, office, or other type of building may include a fire detector to detect a presence of a fire, alert nearby people to the presence of the fire, and/or alert a fire department to the presence of the fire. Various types of fire detectors may be used, such as ionization fire detectors, optical fire detectors, carbon dioxide detectors, and/or the like. However, each type of fire detector may have a deficiency with respect to detection of a fire under a particular type of condition. For example, ionization fire detectors may be relatively poor with respect to detecting slow-smoldering fires that have particulate sizes of greater than approximately 0.4 microns, greater than approximately 10.0 microns, and/or the like; light white or light grey colored smoke; and/or other characteristics. This may result in ionization fire detectors being particularly ill-suited for detecting smoke from gas fires, which may have low concentrations of soot particles but high concentrations of water vapor.

Similarly, optical fire detectors may be relatively poor with respect to detecting fast-flaming fires that have particulate sizes of less than approximately 0.01 microns, less than approximately 0.4 microns, and/or the like. Similarly, carbon dioxide detectors may be relatively poor at early detection of fires when carbon dioxide levels are relatively low. Moreover, the different types of fire detectors may be subject to false alarms (e.g., as a result of non-hazardous conditions, such as a presence of water vapor, dust, or other types of particulates in a proximity to a fire detector) and may be poor at detection of fire in early stages (e.g., when particulate concentrations are relatively low). As a result of poor sensitivities to low concentrations of particulates, current fire detectors may have a delayed response if there is a closed door between a detector and a fire resulting in low air flow and may fail to trigger an alarm until a fire has reached a relatively large size.

Some implementations described herein provide for multispectral sensor based alert condition detection. For example, a multispectral sensor of an optical detector device may perform a spectroscopic measurement across a range of wavelengths, may determine a particulate size of a detected particulate, may determine an identification of the detected particulate, and may determine whether an alert condition is satisfied, such as a fire being present, based on the particulate size and the chemical identification of the detected particulate. In this way, the multispectral sensor may improve an accuracy of fire detection across a range of different fire conditions, relative to other types of fire detector. Moreover, based on using a multispectral sensor in an optical detector device, a size of a fire detector may be reduced to a usable size relative to use of types of spectroscopic devices, which are generally much larger. Furthermore, multispectral sensing may be sensitive to relatively low concentrations of particulate matter with a relatively high degree of accuracy, thereby enabling early fire detection for a wider variety of types of fire with a reduced likelihood of false alarm due to a presence of other particulate matter, water vapor, and/or the like.

Additionally, or alternatively, the optical detector device described herein may perform other types of detection functions. For example, using techniques of particle size and spectroscopic material identification, the optical detector device may perform a detection of air quality, a detection of pollution, a detection of powder sizing, a detection of powder mixing, a particle measurement, a biological measurement, a medical measurement, a cell counting measurement, a water turbidity assessment, and/or the like. In this way, the optical detector device may provide additional functionalities for which fire detectors are not capable, or may be deployed in alternate form factors, such as for controlling a washing machine in a water turbidity use case, providing monitoring in a pollution detection use case, and/or the like.

Figure 1C:
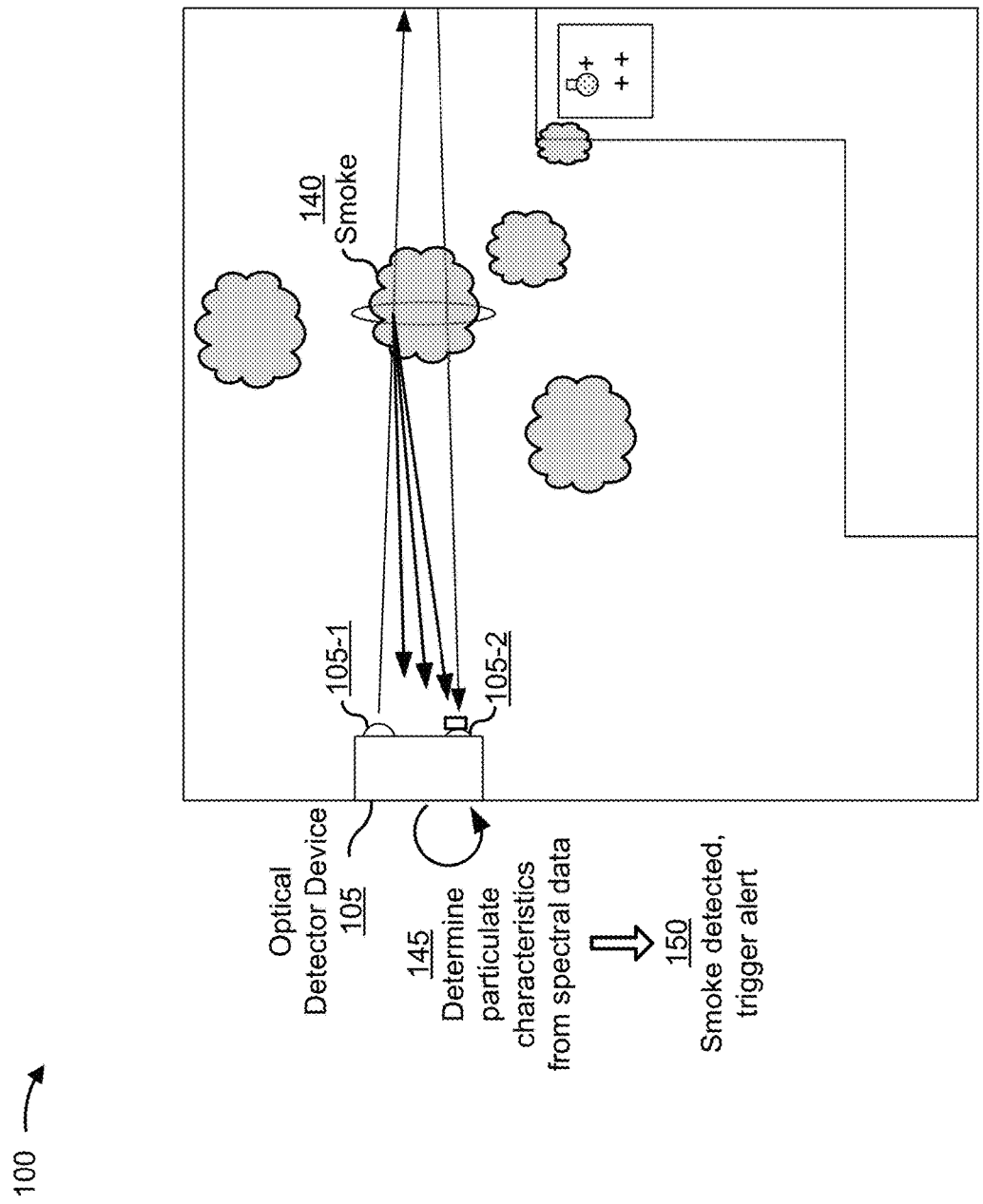

FIGS. 1A-1C are diagrams of an example implementation 100 described herein. As shown in FIGS. 1A-1C, example 100 may include an optical detector device 105. Optical detector device 105 may include an optical transmitter 105-1 and an optical receiver 105-2. In some implementations, a multispectral filter or lens 105-3 may be disposed in an optical path of optical transmitter 105-1 and/or optical receiver 105-2 to filter light, direct light into channels, and/or the like, as described in more detail herein.

As shown in FIG. 1A, and by reference number 115, optical detector device 105 may transmit a beam and may receive a reflection of the beam. For example, the optical transmitter 105-1 may be a light emitting diode (LED) that emits light with a particular wavelength range, and the optical receiver 105-2 may be a sensor element array that receives a reflection of the light with the particular wavelength. In this case, the beam may reflect off a wall in a room and optical detector device 105 may perform a measurement of the beam. For example, optical detector device 105 may determine particulate sizes of any particulates in a path of the beam, an identification of one or more particulates (e.g., every particulate, a subset of particulates, and/or the like) in the path of the beam, an identification of a surface on which the beam is reflected (e.g., a particulate surface, the wall, and/or the like).

In some implementations, optical transmitter 105-1 may provide light in a wavelength range of between 100 nanometers (nm) and 2000 nm, between 190 nm and 1100 nm, between 950 nm and 1650 nm, and/or the like. In some implementations, optical transmitter 105-1 may provide multiple beams. For example, a first LED of optical transmitter 105-1 may provide a first beam with a wavelength range of 190 nm to 650 nm and a second LED of optical transmitter 105-1 may provide a second beam with a wavelength range of 650 nm to 1100 nm. In this case, the first beam and the second beam may be received by a first one or more sensor elements of a sensor element array of optical receiver 105-2 and a second one or more sensor elements of the sensor element array of optical receiver 105-2, respectively.

In some implementations, optical transmitter 105-1 may provide a set of beams associated with a set of channels. For example, optical transmitter 105-1 may provide a set of 32 beams, 64 beams, 128 beams, and/or the like to enable multispectral sensing of a corresponding quantity of wavelengths. In some implementations, optical transmitter 105-1 may provide multiple beams of light with a common wavelength range. For example, optical transmitter 105-1 may provide multiple pulses of the beam to enable multiple spectroscopic measurements to be performed during a measurement period. In some implementations, optical detector device 105 may trigger beam transmission periodically. For example, optical detector device 105 may cause optical transmitter 105-1 to transmit a beam on a 1 second interval, a 5 second interval, a 60 second interval, and/or the like. In some implementations, optical detector device 105 may cause optical transmitter 105-1 to transmit the beam on a non-periodic basis. For example, based on detecting an alert condition, optical detector device 105 may cause optical transmitter 105-1 to transmit one or more beams to verify the alert condition, track changes to the alert condition (e.g., a rate of increase of a fire), and/or the like.

Although some implementations are described in terms of transmission of light through a gaseous medium (e.g., air) other mediums are possible. For example, to detect an alert condition relating to a water turbidity (e.g., to detect whether a threshold amount of dirt is present in water, such as greater than a threshold to continue a cleaning cycle or less than a threshold to end a cleaning cycle), optical detector device 105 may transmit light through a liquid medium. In this case, optical detector device 105 may determine, for example, that a concentration of particulates classified as dirt particles is less than a threshold, and may communicate with a control unit of, for example, a washing machine or dishwasher to indicate an alert condition (e.g., to end a wash cycle).

In some implementations, optical detector device 105 may perform a particulate size determination. For example, based at least in part on a range of wavelengths reflected back to optical detector device 105, optical detector device 105 may determine a size of a set of particulates in an optical path of optical detector device 105. In some implementations, optical detector device 105 may perform a particulate size determination on multiple types of particulates. For example, using spectroscopic analysis, optical detector device 105 may determine multiple particulate sizes and identify multiple types of particulates using a single set of spectroscopic measurements. In some implementations, optical detector device 105 may determine a particulate concentration determination based on a range of wavelengths reflected back to optical detector device 105.

In some implementations, optical detector device 105 may perform an identification on particulates in the path of the beam. For example, optical detector device 105 may identify a spectrum of a particulate that reflected the beam and may classify the spectrum of the particulate into a particular class using a spectroscopic classification model. In this case, optical detector device 105 may determine that detected particulate matter includes, for example, a dust particle, a water vapor particle, a pollen particle, and/or the like.

Additionally, or alternatively, optical detector device 105 may determine a spectrum of, for example, a wall that reflected the beam, an inner surface of a housing of optical detector device 105 that reflected the beam, and/or the like. For example, when the light is reflected off a wall, optical detector device 105 may determine that reflected light has a spectrum that matches a spectrum of the wall, and may determine that a fire is not occurring and causing particulate matter to be disposed between optical detector device 105 and the wall. Additionally, or alternatively, when optical detector device 105 includes a housing and an inflow device to draw air and particulate matter into a volume of the housing, optical detector device 105 may determine that a received spectrum matches a spectrum of a surface of the housing, which may indicate that air that is drawn into the volume of the housing does not include particulate matter indicative of a fire occurring.

In some implementations, based on a size of one or more detected particulates, a concentration of the one or more detected particulates, an identification of the one or more detected particulates, and/or the like, optical detector device 105 may determine that there is no indication of a fire. For example, optical detector device 105 may determine that an alert condition is not satisfied based on a type, size, concentration, and/or the like of detected particulates not satisfying a set of criteria for detecting a fire. In this case, as shown by reference number 120, based on determining that the alert condition is not satisfied, optical detector device 105 may not trigger an alert.

As shown in FIG. 1B, and by reference number 125, in another case, optical detector device 105 may transmit a beam and steam may be disposed in an optical path of the beam. As shown by reference number 130, optical detector device 105 may determine, based on spectral data from a spectroscopic measurement, particulate characteristics of particulate matter that has reflected the beam. For example, based on a spectroscopic measurement of a spectrum of the reflected beam, optical detector device 105 may determine a particulate size, a particulate identification, a particulate concentration, and/or the like. In this case, optical detector device 105 may determine that the particulate size and the particulate identification indicates a presence of water vapor from cooking rather than, for example, water vapor associated with a gas fire. For example, optical detector device 105 may determine that trace elements detected based on a spectroscopic measurement result in classifying the spectroscopic measurement as being of water vapor from cooking (e.g., which may include first trace elements) rather than water vapor from a gas fire (e.g., which may include second trace elements).

As further shown in FIG. 1B, and by reference number 135, optical detector device 105 may determine that an alert condition is not satisfied based on the spectral data. For example, optical detector device 105 may determine that water vapor from cooking does not satisfy an alert condition for identifying a fire, and may refrain from triggering an alert. In some implementations, optical detector device 105 may use a predictive model to determine whether the alert condition is satisfied. For example, optical detector device 105 may receive a predictive model trained using training data of spectra from cooking-based water vapor and gas fire-based water vapor (e.g., which may be associated with different concentrations, different particulate sizes, different trace elements in addition to water vapor, and/or the like), and may determine that detected particulate sizes, concentrations, and identities indicate a cooking event rather than an occurrence of a fire. In this way, optical detector device 105 reduces a likelihood of a false alarm.

As shown in FIG. 1C, and by reference number 140, in another case, optical detector device 105 may transmit a beam and smoke from a fire may be disposed in an optical path of the reflected beam. As shown by reference number 145, optical detector device 105 may determine particulate characteristics based on spectral data of a spectroscopic measurement. For example, based on a spectroscopic measurement of a spectrum of the reflected beam, optical detector device 105 may determine a particulate size, a particulate concentration, a particulate identification, and/or the like of particulates that reflected the beam back to optical detector device 105. Based on the particulate characteristics, optical detector device 105 may determine that the reflected beam is in a presence of smoke from a fire. For example, optical detector device 105 may detect a presence of soot, smoke, carbon dioxide, water vapor, and/or the like in concentrations and/or with particulate sizes corresponding to characteristics of a fire. In some implementations, optical detector device 105 may use a predictive model to determine that the spectra correspond to the presence of a fire. For example, optical detector device 105 may classify a single spectrum (e.g., a spectrum of a single particulate), a plurality of spectra (e.g., a plurality of spectra of a plurality of particulates), and/or the like as corresponding to a particular class that is indicative of a fire occurring. In some implementations, optical detector device 105 may use a support vector machine (SVM) technique to classify a spectrum into a particular class using a spectroscopic model.

In some implementations, optical detector device 105 may perform a binary classification. For example, optical detector device 105 may classify a spectrum as indicating that an alert condition is satisfied (e.g., a fire is occurring) or indicating that the alert condition is not satisfied (e.g., a fire is not occurring). In some implementations, optical detector device 105 may perform a non-binary classification. For example, optical detector device 105 may classify a spectrum into a particular type of fire associated with a particular chemometric signature (e.g., an electrical fire may have a first chemometric signature, a chemical fire may have a second chemometric signature, a gas fire may have a third chemometric signature, and/or the like). Additionally, or alternatively, optical detector device 105 may classify the spectrum into a particular type of non-fire hazardous event (e.g., a threshold level of carbon dioxide, carbon monoxide, pollution, pollen, dust, and/or the like), a particular type of non-hazardous event (e.g., a presence of steam, a non-hazardous concentration of dust, and/or the like), and/or the like. Additionally, or alternatively, in other use cases, optical detector device 105 may perform a classification regarding a water turbidity, an alert regarding a cell count, an alert regarding a medical condition, and/or the like.

As further shown in FIG. 1C, and by reference number 150, optical detector device 105 may trigger an alert. For example, optical detector device 105 may provide an audio alert, a visual alert, a tactile alert (e.g., a vibration), and/or the like to indicate that the alert condition is satisfied (e.g., that there is a fire detected). In some implementations, optical detector device 105 may communicate with another device to provide an alert. For example, optical detector device 105 may transmit an indication of the alert condition to a dispatch device or emergency responder device of an emergency response service or a fire station.

In some implementations, optical detector device 105 may provide contextual information regarding the alert condition. For example, optical detector device 105 may provide information identifying a type of fire (e.g., a gas fire, a chemical fire, an electrical fire, and/or the like) to enable a response to the fire that is targeted to the type of fire. Additionally, or alternatively, optical detector device 105 may provide information identifying a size of the fire (e.g., based on a concentration of particulates, a type of particulate, a size of particulate, and/or the like). Additionally, or alternatively, optical detector device 105 may provide information identifying a growth rate of the fire based on spectral measurements over a period of time.

In some implementations, optical detector device 105 may log information regarding the alert condition. For example, optical detector device 105 may log the spectra, a type of the fire, a growth rate of the fire, a type of alert provided, and/or the like, thereby enabling subsequent diagnostics, model refining, insurance evaluation, and/or the like. In this way, optical detector device 105 enables accurate fire detection.

As indicated above, FIGS. 1A-1C are provided merely as one or more examples. Other examples may differ from what is described with regard to FIGS. 1A-1C.

Figure 2:
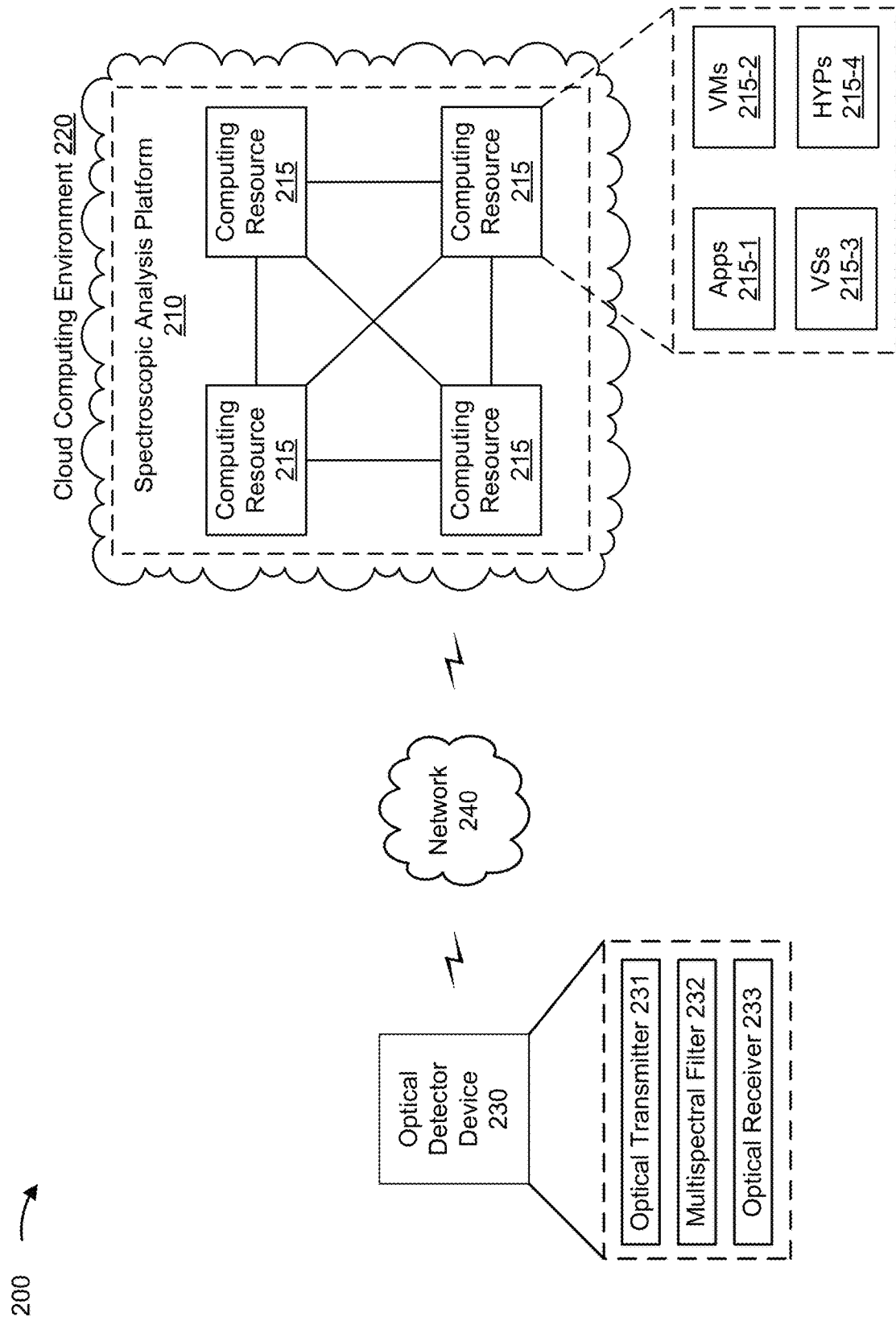
FIG. 2 is a diagram of an example environment in which systems and/or methods described herein may be implemented.

FIG. 2 is a diagram of an example environment 200 in which systems and/or methods described herein may be implemented. As shown in FIG. 2, environment 200 may include a spectroscopic analysis platform 210, a computing resource 215, a cloud computing environment 220, a optical detector device 230, and a network 240. Devices of environment 200 may interconnect via wired connections, wireless connections, or a combination of wired and wireless connections.

Spectroscopic analysis platform 210 includes one or more computing resources assigned to analyze a spectroscopic measurement. For example, spectroscopic analysis platform 210 may be a platform implemented by cloud computing environment 220 that may analyze a spectroscopic measurement performed by optical detector device 230 and provide a result of analyzing the spectroscopic measurement. In some implementations, spectroscopic analysis platform 210 is implemented by computing resources 215 of cloud computing environment 220.

Spectroscopic analysis platform 210 may include a server device or a group of server devices. In some implementations, spectroscopic analysis platform 210 may be hosted in cloud computing environment 220. Notably, while implementations described herein may describe spectroscopic analysis platform 210 as being hosted in cloud computing environment 220, in some implementations, spectroscopic analysis platform 210 may be non-cloud-based or may be partially cloud-based.

Cloud computing environment 220 includes an environment that delivers computing as a service, whereby shared resources, services, and/or the like may be provided to analyze a spectroscopic measurement. Cloud computing environment 220 may provide computation, software, data access, storage, and/or other services that do not require end-user knowledge of a physical location and configuration of a system and/or a device that delivers the services. As shown, cloud computing environment 220 may include spectroscopic analysis platform 210 and a computing resource 215.

Computing resource 215 includes one or more personal computers, workstation computers, server devices, or another type of computation and/or communication device. In some implementations, computing resource 215 may host spectroscopic analysis platform 210. The cloud resources may include compute instances executing in computing resource 215, storage devices provided in computing resource 215, data transfer devices provided by computing resource 215, and/or the like. In some implementations, computing resource 215 may communicate with other computing resources 215 via wired connections, wireless connections, or a combination of wired and wireless connections.

As further shown in FIG. 2, computing resource 215 may include a group of cloud resources, such as one or more applications ("APPs") 215-1, one or more virtual machines ("VMs") 215-2, virtualized storage ("VSs") 215-3, one or more hypervisors ("HYPs") 215-4, or the like.

Application 215-1 includes one or more software applications that may be provided to or accessed by optical detector device 230. Application 215-1 may eliminate a need to install and execute the software applications on optical detector device 230. For example, application 215-1 may include software associated with spectroscopic analysis platform 210 and/or any other software capable of being provided via cloud computing environment 220. In some implementations, one application 215-1 may send/receive information to/from one or more other applications 215-1, via virtual machine 215-2.

Virtual machine 215-2 includes a software implementation of a machine (e.g., a computer) that executes programs like a physical machine. Virtual machine 215-2 may be either a system virtual machine or a process virtual machine, depending upon use and degree of correspondence to any real machine by virtual machine 215-2. A system virtual machine may provide a complete system platform that supports execution of a complete operating system ("OS"). A process virtual machine may execute a single program and may support a single process. In some implementations, virtual machine 215-2 may execute on behalf of a user (e.g., optical detector device 230), and may manage infrastructure of cloud computing environment 220, such as data management, synchronization, or long-duration data transfers.

Virtualized storage 215-3 includes one or more storage systems and/or one or more devices that use virtualization techniques within the storage systems or devices of computing resource 215. In some implementations, within the context of a storage system, types of virtualizations may include block virtualization and file virtualization. Block virtualization may refer to abstraction (or separation) of logical storage from physical storage so that the storage system may be accessed without regard to physical storage or heterogeneous structure. The separation may permit administrators of the storage system flexibility in how the administrators manage storage for end users. File virtualization may eliminate dependencies between data accessed at a file level and a location where files are physically stored. This may enable optimization of storage use, server consolidation, and/or performance of non-disruptive file migrations.

Hypervisor 215-4 provides hardware virtualization techniques that allow multiple operating systems (e.g., "guest operating systems") to execute concurrently on a host computer, such as computing resource 215. Hypervisor 215-4 may present a virtual operating platform to the guest operating systems and may manage the execution of the guest operating systems. Multiple instances of a variety of operating systems may share virtualized hardware resources.

Optical detector device 230 includes one or more devices capable of receiving, generating, storing, processing, and/or providing information associated with analyzing a spectroscopic measurement. For example, optical detector device 230 may include an optical transmitter to transmit a beam with a range of wavelengths, a multispectral filter or lens to direct a reflection of the beam into multiple channels, an optical receiver including a sensor element array to receive a reflection of the beam via the multiple channels, and/or the like.

In some implementations, optical detector device 230 may include an optical transmitter 231, a multispectral filter 232, an optical receiver 233, and/or the like. Optical transmitter 231 may be an LED, a laser, or another type of device to provide a beam with a range of wavelengths. Multispectral filter 232 (e.g., a binary multispectral filter) may be a filter disposed in an optical path of optical transmitter 231 and/or optical receiver 233 to filter a beam. For example, multispectral filter 232 may include multiple areas to selectively block wavelengths of the beam to divide the beam into a discrete set of channels for sensing by a sensor element array of optical receiver 233. In this case, multispectral filter 232 may have 32 channels, 64 channels, 128 channels, and/or the like. Additionally, or alternatively, any other quantity of channels may be possible, such as 31 channels, 33 channels, 100 channels, and/or the like. Optical receiver 233 may include a photodiode, a sensor element, a sensor element array, and/or the like which may receive a beam and perform a measurement of a wavelength of the beam.

In some implementations, optical detector device 230 includes a housing with an opening and an inflow device. For example, optical detector device 230 may use the inflow device (e.g., a fan) to draw fluid (e.g., air, water, and/or the like) into the housing to enable a spectroscopic measurement to be performed within the housing. In some implementations, optical detector device 230 may be configured as a fixed angle multispectral sensor device. In some implementations, optical detector device 230 may be included in a communication and/or computing device, such as a mobile phone (e.g., a smart phone, a radiotelephone, etc.), a laptop computer, a tablet computer, a handheld computer, a desktop computer, a gaming device, a wearable communication device (e.g., a smart wristwatch, a pair of smart eyeglasses, etc.), or a similar type of device.

Network 240 includes one or more wired and/or wireless networks. For example, network 240 may include a cellular network (e.g., a long-term evolution (LTE) network, a code division multiple access (CDMA) network, a 3G network, a 4G network, a 5G network, another type of next generation network, and/or the like), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, a cloud computing network, and/or the like, and/or a combination of these or other types of networks.

The number and arrangement of devices and networks shown in FIG. 2 are provided as one or more examples. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices) of environment 200 may perform one or more functions described as being performed by another set of devices of environment 200.

Figure 3:
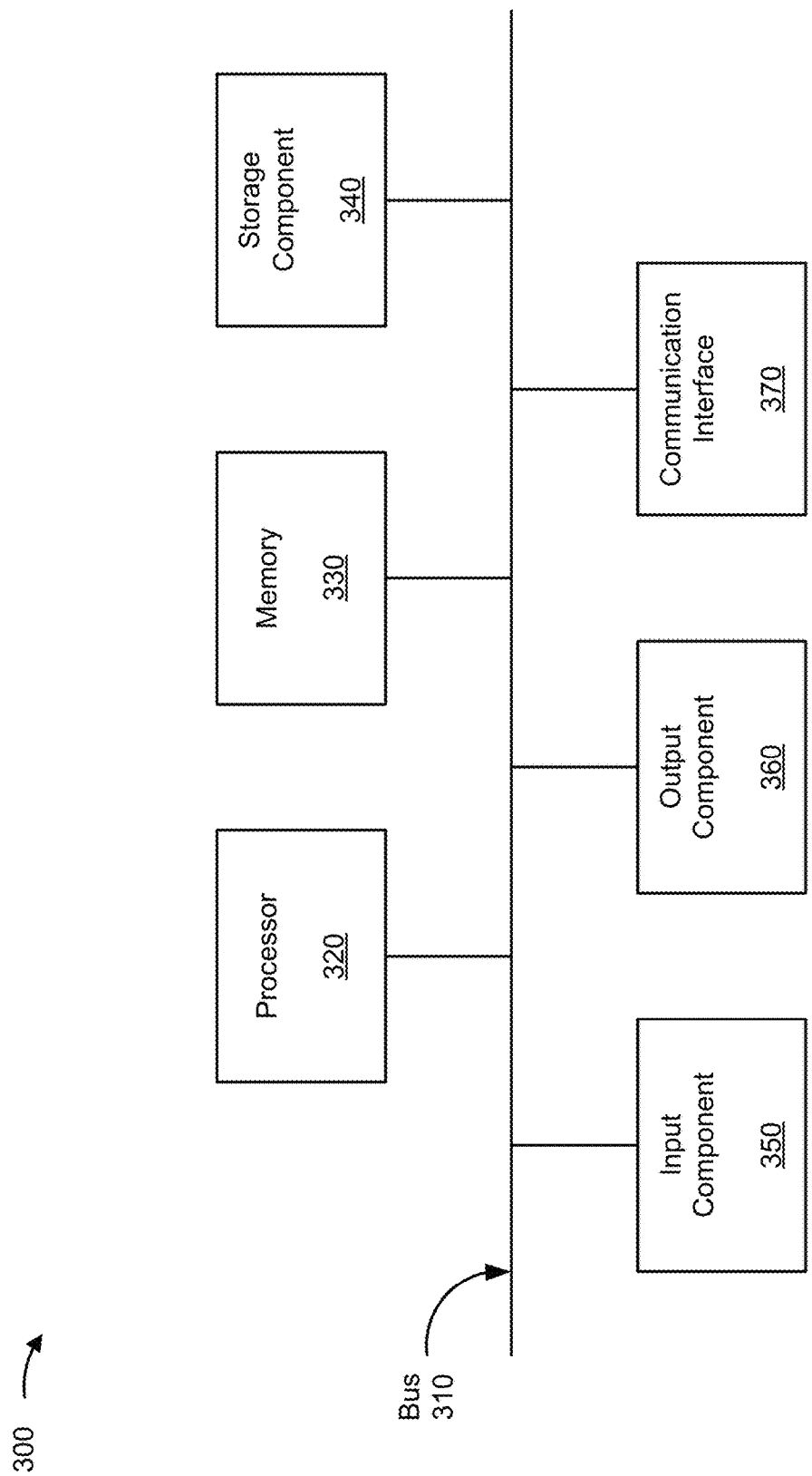
FIG. 3 is a diagram of example components of one or more devices of FIG. 2.

FIG. 3 is a diagram of example components of a device 300. Device 300 may correspond to spectroscopic analysis platform 210, computing resource 215, and/or optical detector device 230. In some implementations, spectroscopic analysis platform 210, computing resource 215, and/or optical detector device 230 may include one or more devices 300 and/or one or more components of device 300. As shown in FIG. 3, device 300 may include a bus 310, a processor 320, a memory 330, a storage component 340, an input component 350, an output component 360, and/or a communication interface 370.

Bus 310 includes a component that permits communication among multiple components of device 300. Processor 320 is implemented in hardware, firmware, and/or a combination of hardware and software. Processor 320 takes the form of a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 320 includes one or more processors capable of being programmed to perform a function. Memory 330 includes a random access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operation and use of device 300. For example, storage component 340 may include a hard disk (e.g., a magnetic disk, an optical disk, and/or a magneto-optic disk), a solid state drive (SSD), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a component for determining location (e.g., a global positioning system (GPS) component) and/or a sensor (e.g., an accelerometer, a gyroscope, an actuator, another type of positional or environmental sensor, and/or the like). Output component 360 includes a component that provides output information from device 300 (via, e.g., a display, a speaker, a haptic feedback component, an audio or visual indicator, and/or the like).

Communication interface 370 includes a transceiver-like component (e.g., a transceiver, a separate receiver, a separate transmitter, and/or the like) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, and/or the like.

Device 300 may perform one or more processes described herein. Device 300 may perform these processes based on processor 320 executing software instructions stored by a non-transitory computer-readable medium, such as memory 330 and/or storage component 340. As used herein, the term "computer-readable medium" refers to a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardware circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
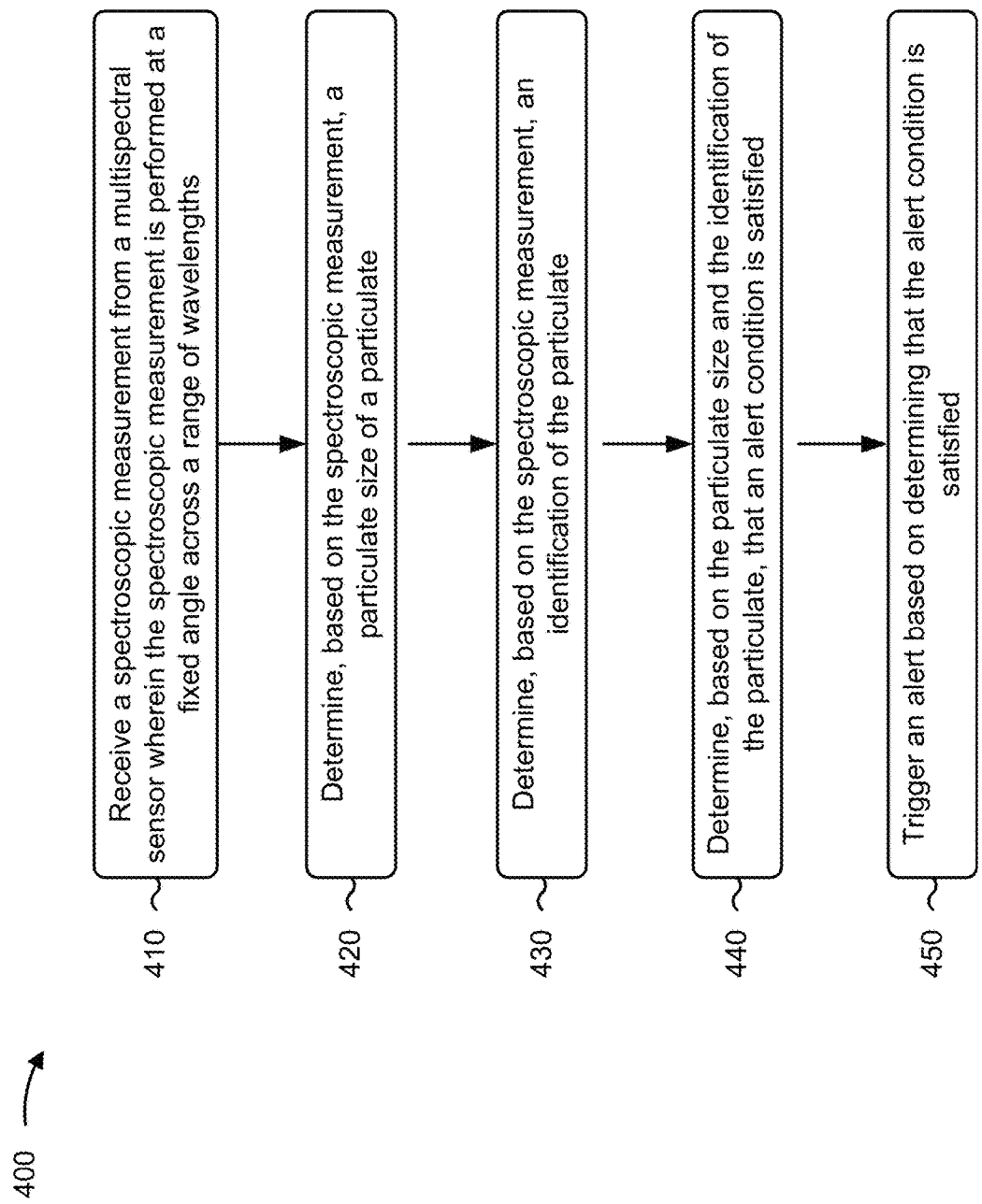
FIGS. 4-6 are flowcharts of example processes for detecting an alert condition using a multispectral sensor.

FIG. 4 is a flow chart of an example process 400 for detecting an alert condition. In some implementations, one or more process blocks of FIG. 4 may be performed by an optical detector device (e.g., optical detector device 230). In some implementations, one or more process blocks of FIG. 4 may be performed by another device or a group of devices separate from or including the optical detector device, such as a spectroscopic analysis platform (e.g., spectroscopic analysis platform 210) and/or the like.

As shown in FIG. 4, process 400 may include receiving a spectroscopic measurement from a multispectral sensor wherein the spectroscopic measurement is performed at a fixed angle across a range of wavelengths (block 410). For example, the optical detector device (e.g., using processor 320, memory 330, storage component 340, input component 350, output component 360, communication interface 370 and/or the like) may receive a spectroscopic measurement from a multispectral sensor, as described above. In some implementations, the spectroscopic measurement is performed at a fixed angle across a range of wavelengths.

As further shown in FIG. 4, process 400 may include determining, based on the spectroscopic measurement, a particulate size of a particulate (block 420). For example, the optical detector device (e.g., using processor 320, memory 330, storage component 340, input component 350, output component 360, communication interface 370 and/or the like) may determine, based on the spectroscopic measurement, a particulate size of a particulate, as described above.

As further shown in FIG. 4, process 400 may include determining, based on the spectroscopic measurement, an identification of the particulate (block 430). For example, the optical detector device (e.g., using processor 320, memory 330, storage component 340, input component 350, output component 360, communication interface 370 and/or the like) may determine, based on the spectroscopic measurement, an identification of the particulate, as described above.

As further shown in FIG. 4, process 400 may include determining, based on the particulate size and the identification of the particulate, that an alert condition is satisfied (block 440). For example, the optical detector device (e.g., using processor 320, memory 330, storage component 340, input component 350, output component 360, communication interface 370 and/or the like) may determine, based on the particulate size and the identification of the particulate, that an alert condition is satisfied, as described above.

As further shown in FIG. 4, process 400 may include triggering an alert based on determining that the alert condition is satisfied (block 450). For example, the optical detector device (e.g., using processor 320, memory 330, storage component 340, input component 350, output component 360, communication interface 370 and/or the like) may trigger an alert based on determining that the alert condition is satisfied, as described above.

Process 400 may include additional implementations, such as any single implementation or any combination of implementations described below and/or in connection with one or more other processes described elsewhere herein.

In a first implementation, process 400 includes determining one or more other particulate sizes of one or more other particulates; determining one or more other identifications of the one or more other particulates; and determining that the alert condition is satisfied based on the one or more other particulate sizes and the one or more other identifications of the one or more other particulates.

In a second implementation, alone or in combination with the first implementation, process 400 includes transmitting an instruction to cause a beam to be provided with the range of wavelengths; and receiving the spectroscopic measurement as a response to transmitting the instruction.

In a third implementation, alone or in combination with one or more of the first and second implementations, the one or more processors, process 400 includes determining, using a spectroscopic classification model, a classification of a spectrum of the particulate based on the spectroscopic measurement; and determining the identification of the particulate based on the classification of the spectrum of the particulate.

In a fourth implementation, alone or in combination with one or more of the first through third implementations, process 400 includes determining, based on the particulate size and the identification of the particulate, that a fire is occurring within a proximity of the multispectral sensor.

In a fifth implementation, alone or in combination with one or more of the first through fourth implementations, process 400 includes determining, based on the spectroscopic measurement, a chemometric signature of the fire based on determining that the fire is occurring within the proximity of the multispectral sensor; and providing information identifying the chemometric signature.

In a sixth implementation, alone or in combination with one or more of the first through fifth implementations, process 400 includes triggering an audible or visual alert to indicate the alert condition.

In a seventh implementation, alone or in combination with one or more of the first through sixth implementations, process 400 includes communicating with an emergency responder device to indicate the alert condition.

In an eighth implementation, alone or in combination with one or more of the first through seventh implementations, process 400 includes determining, based on the particulate size and the identification of the particulate, that the particulate is smoke-based particulate; and determining that the smoke-based particulate is a first type of smoke-based particulate that satisfies the alert condition rather than a second type of smoke-based particulate that does not satisfy the alert condition.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

Figure 5:
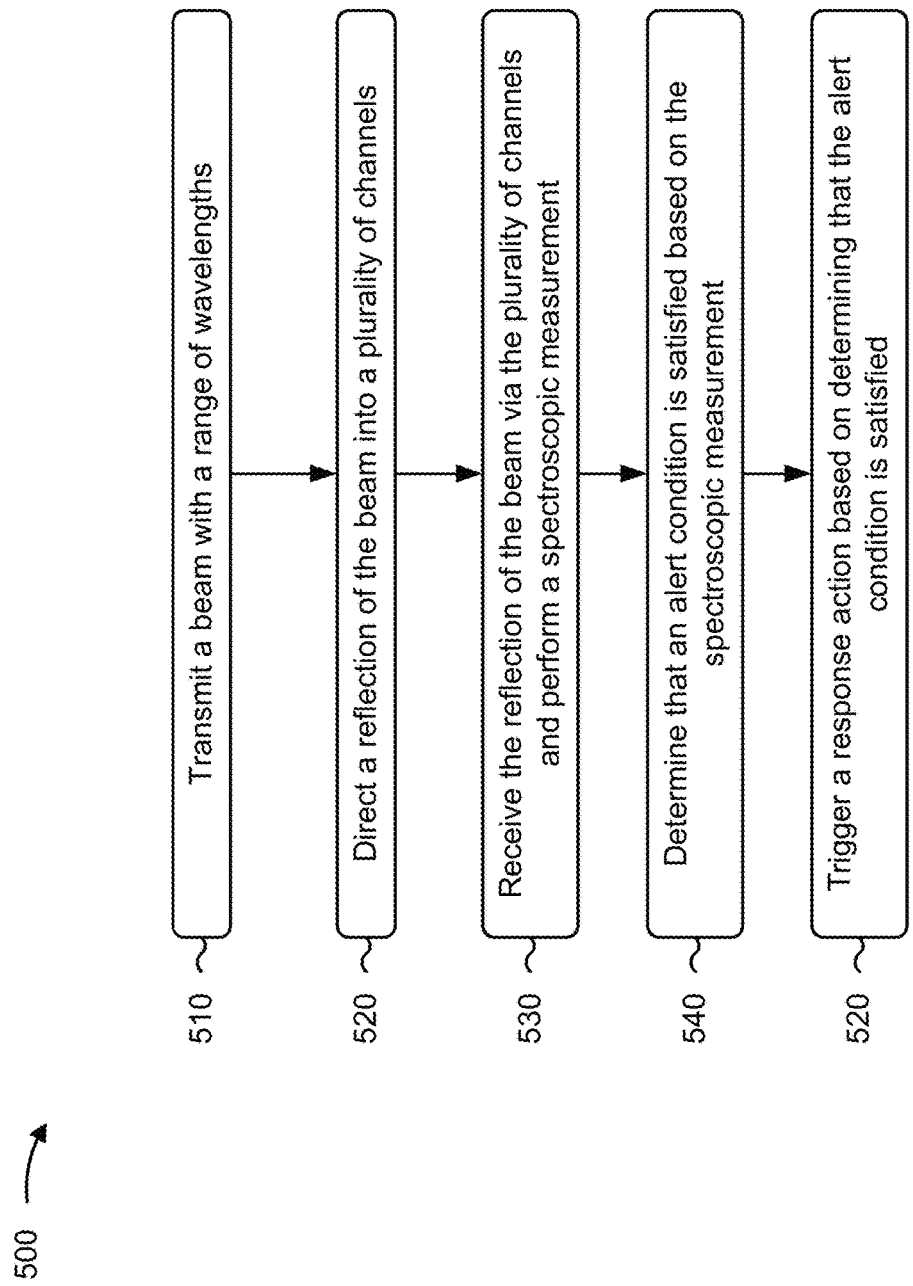

FIG. 5 is a flow chart of an example process 500 for detecting an alert condition. In some implementations, one or more process blocks of FIG. 5 may be performed by an optical detector device (e.g., optical detector device 230). In some implementations, one or more process blocks of FIG. 5 may be performed by another device or a group of devices separate from or including the optical detector device, such as a spectroscopic analysis platform (e.g., spectroscopic analysis platform 210) and/or the like.

As shown in FIG. 5, process 500 may include transmitting a beam with a range of wavelengths (block 510). For example, the optical detector device (e.g., using optical transmitter 231) may transmit a beam with a range of wavelengths, as described above.

As further shown in FIG. 5, process 500 may include directing a reflection of the beam into a plurality of channels (block 520). For example, the optical detector device (e.g., using multispectral filter 232) may direct a reflection of the beam into a plurality of channels, as described above.

As further shown in FIG. 5, process 500 may include receiving the reflection of the beam via the plurality of channels and performing a spectroscopic measurement (block 530). For example, the optical detector device (e.g., using a sensor element array of optical receiver 233) may receive the reflection of the beam via the plurality of channels and perform a spectroscopic measurement, as described above.

As further shown in FIG. 5, process 500 may include determining that an alert condition is satisfied, based on the spectroscopic measurement (block 540). For example, the optical detector device (e.g., using processor 320, memory 330, storage component 340, input component 350, output component 360, communication interface 370 and/or the like) may determine that an alert condition is satisfied, based on the spectroscopic measurement, as described above.

As further shown in FIG. 5, process 500 may include triggering a response action based on determining that the alert condition is satisfied (block 520). For example, the optical detector device (e.g., using processor 320, memory 330, storage component 340, input component 350, output component 360, communication interface 370 and/or the like) may trigger a response action based on determining that the alert condition is satisfied, as described above.

Process 500 may include additional implementations, such as any single implementation or any combination of implementations described below and/or in connection with one or more other processes described elsewhere herein.

In a first implementation, the range of wavelengths is from 190 nm to 1100 nm.

In a second implementation, alone or in combination with the first implementation, a first light emitter may transmit a first portion of the beam with a first portion of the range of wavelengths and a second light emitter may transmit a second portion of the beam with a second portion of the range of wavelengths.

In a third implementation, alone or in combination with one or more of the first and second implementations, the sensor element array includes a first one or more sensor elements to receive a first portion of the reflection of the beam with a first portion of the range of wavelengths and a second one or more sensor elements to receive a second portion of the reflection of the beam with a second portion of the range of wavelengths.

In a fourth implementation, alone or in combination with one or more of the first through third implementations, the optical transmitter is configured to transmit the beam, through a medium, toward particulates in the medium. In some implementations, the medium is a gaseous medium or a liquid medium.

In a fifth implementation, alone or in combination with one or more of the first through fourth implementations, the optical detector device may include a housing with an opening and a particulate inflow device to draw fluid from a first environment external to the housing to a second environment internal to the housing via the opening, and the optical transmitter is configured to transmit the beam, and the optical receiver is configured to receive the reflection of the beam, within the second environment internal to the housing.

In a sixth implementation, alone or in combination with one or more of the first through fifth implementations, a sensitivity of the optical receiver is for particulates with a concentration of less than a threshold.

Although FIG. 5 shows example blocks of process 500, in some implementations, process 500 may include additional blocks, fewer blocks, different blocks, or differently arranged blocks than those depicted in FIG. 5. Additionally, or alternatively, two or more of the blocks of process 500 may be performed in parallel.

Figure 6:
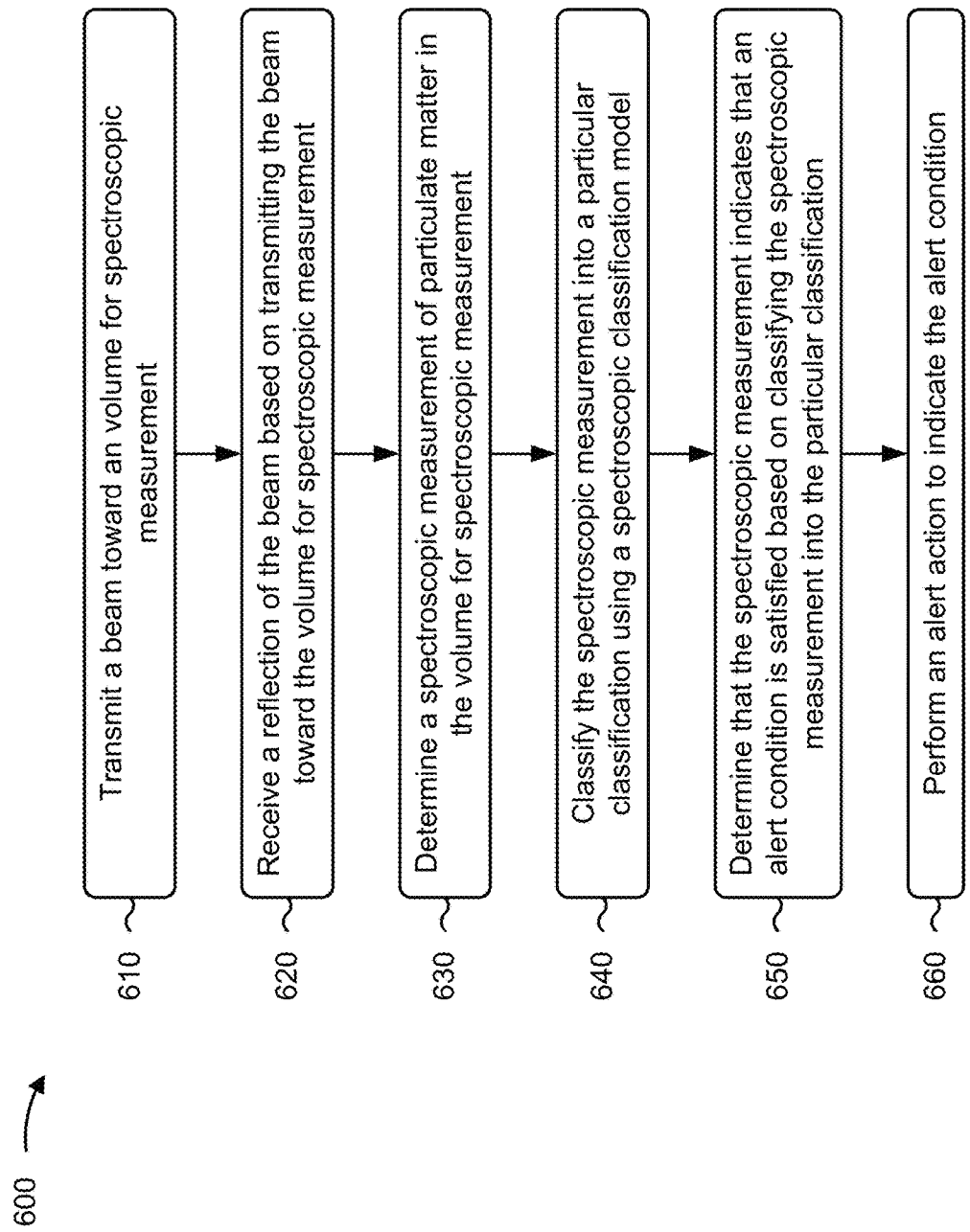

FIG. 6 is a flow chart of an example process 600 for detecting an alert condition. In some implementations, one or more process blocks of FIG. 6 may be performed by an optical detector device (e.g., optical detector device 230). In some implementations, one or more process blocks of FIG. 6 may be performed by another device or a group of devices separate from or including the optical detector device, such as a spectroscopic analysis platform (e.g., spectroscopic analysis platform 210) and/or the like.

As shown in FIG. 6, process 600 may include transmitting a beam toward a volume for spectroscopic measurement (block 610). For example, the optical detector device (e.g., using processor 320, memory 330, storage component 340, input component 350, output component 360, communication interface 370 and/or the like) may transmit a beam toward a volume for spectroscopic measurement, as described above.

As further shown in FIG. 6, process 600 may include receiving a reflection of the beam based on transmitting the beam toward the volume for spectroscopic measurement (block 620). For example, the optical detector device (e.g., using processor 320, memory 330, storage component 340, input component 350, output component 360, communication interface 370 and/or the like) may receive a reflection of the beam based on transmitting the beam toward the volume for spectroscopic measurement, as described above.

As further shown in FIG. 6, process 600 may include determining a spectroscopic measurement of particulate matter in the volume for spectroscopic measurement (block 630). For example, the optical detector device (e.g., using processor 320, memory 330, storage component 340, input component 350, output component 360, communication interface 370 and/or the like) may determine a spectroscopic measurement of particulate matter in the volume for spectroscopic measurement, as described above.

As further shown in FIG. 6, process 600 may include classifying the spectroscopic measurement into a particular classification using a spectroscopic classification model (block 640). For example, the optical detector device (e.g., using processor 320, memory 330, storage component 340, input component 350, output component 360, communication interface 370 and/or the like) may classify the spectroscopic measurement into a particular classification using a spectroscopic classification model, as described above.

As further shown in FIG. 6, process 600 may include determining that the spectroscopic measurement indicates that an alert condition is satisfied based on classifying the spectroscopic measurement into the particular classification (block 650). For example, the optical detector device (e.g., using processor 320, memory 330, storage component 340, input component 350, output component 360, communication interface 370 and/or the like) may determine that the spectroscopic measurement indicates that an alert condition is satisfied based on classifying the spectroscopic measurement into the particular classification, as described above.

As further shown in FIG. 6, process 600 may include performing an alert action to indicate the alert condition (block 660). For example, the optical detector device (e.g., using processor 320, memory 330, storage component 340, input component 350, output component 360, communication interface 370 and/or the like) may perform an alert action to indicate the alert condition, as described above.

Process 600 may include additional implementations, such as any single implementation or any combination of implementations described below and/or in connection with one or more other processes described elsewhere herein.

In a first implementation, performing the alert action includes providing an alert regarding a fire, providing an alert regarding a pollution condition, providing an alert regarding an air quality condition, providing an indication of a medical condition, or altering a setting of a device based on a water turbidity condition.

In a second implementation, alone or in combination with the first implementation, process 600 includes logging information regarding the spectroscopic measurement; and providing, at a subsequent time, an output of a log storing the logged information regarding the spectroscopic measurement.

In a third implementation, alone or in combination with one or more of the first and second implementations, classifying the spectroscopic measurement includes classifying the spectroscopic measurement based on at least one of a size of the particulate matter, a concentration of the particulate matter, or a type of the particulate matter.

Although FIG. 6 shows example blocks of process 600, in some implementations, process 600 may include additional blocks, fewer blocks, different blocks, or differently arranged blocks than those depicted in FIG. 6. Additionally, or alternatively, two or more of the blocks of process 600 may be performed in parallel.

FIGS. 7A and 7B are diagrams of an example implementation 700 described herein.

As shown in FIG. 7A, an optical detector device may include an optical transmitter 702, an optical receiver 704, a filter 706 (e.g., a multispectral filter), and a housing 708. Optical receiver 704 and filter 706 may form a multispectral sensor. Optical transmitter 702 may transmit beam 710, which may be reflected off a surface of housing 708 toward optical receiver 704. Housing 708 may include an opening to enable air inflow and an opening to enable air outflow, thereby enabling fixed angle sensing.

As shown in FIG. 7B, the multispectral sensor formed by optical receiver 704 and filter 706 may include a substrate 752, a set of sensor elements 754 disposed on or in substrate 752, and a set of filter layers 756 disposed on the set of sensor elements 754. In some implementations, filter layers 756 may include a first subset of layers of a first material and a second subset of layers of a second material. For example, filter layers 756 may include alternating high refractive index and low refractive index layers to form a set of channels corresponding to the set of sensor elements 754. In some implementations, a subset of filter layers 756 may be associated with a refractive index greater than 2.5, greater than 3.0, greater than 3.5, and/or the like. In some implementations, a subset of filter layers 756 may be associated with a refractive index less than 2.5, less than 2.0, less than 1.5, and/or the like. In some implementations, filter layers 756 may include silicon layers, hydrogenated silicon layers, silicon-germanium (SiGe) layers, hydrogenated germanium layers, hydrogenated silicon-germanium layers, silicon dioxide layers, tantalum pentoxide ($Ta_2O_5$) layers, niobium pentoxide ($Nb_2O_5$) layers, titanium dioxide ($TiO_2$) layers, aluminum oxide ($Al_2O_3$) layers, zirconium oxide ($ZrO_2$) layers, yttrium oxide ($Y_2O_3$) layers, silicon nitride ($Si_3N_4$) layers, magnesium fluoride ($MgF_2$) layers, niobium titanium fluoride (NbTiF) layers, niobium titanium oxide (NbTiO) layers, an anion/cation mixture layer, a hydrogenated layer, an annealed layer, an etched layer, a deposited layer, a combination thereof, and/or the like.

As indicated above, FIGS. 7A and 7B are provided merely as one or more examples. Other examples may differ from what is described with regard to FIGS. 7A and 7B.

The foregoing disclosure provides illustration and description, but is not intended to be exhaustive or to limit the implementations to the precise forms disclosed. Modifications and variations may be made in light of the above disclosure or may be acquired from practice of the implementations.

As used herein, the term "component" is intended to be broadly construed as hardware, firmware, and/or a combination of hardware and software.

Some implementations are described herein in connection with thresholds. As used herein, satisfying a threshold may, depending on the context, refer to a value being greater than the threshold, more than the threshold, higher than the threshold, greater than or equal to the threshold, less than the threshold, fewer than the threshold, lower than the threshold, less than or equal to the threshold, equal to the threshold, or the like.

It will be apparent that systems and/or methods described herein may be implemented in different forms of hardware, firmware, or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Further, as used herein, the article "the" is intended to include one or more items referenced in connection with the article "the" and may be used interchangeably with "the one or more." Furthermore, as used herein, the term "set" is intended to include one or more items (e.g., related items, unrelated items, a combination of related and unrelated items, etc.), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

What is claimed is:

1. An optical detector device, comprising:
one or more memories; and
one or more processors, communicatively coupled to the one or more memories, to:
receive a spectroscopic measurement from a multispectral sensor, wherein the spectroscopic measurement is performed at a fixed angle across a range of wavelengths;
determine, based on the spectroscopic measurement, a particulate size of a particulate;
determine, based on the spectroscopic measurement, an identification of the particulate;
determine, based on the particulate size and the identification of the particulate, that the particulate is a smoke-based particulate;
determine that an alert condition is satisfied based on the smoke-based particulate being a first type of smoke-based particulate that satisfies the alert condition, the first type of smoke-based particulate being different from a second type of smoke-based particulate that does not satisfy the alert condition; and
trigger an alert based on determining that the alert condition is satisfied.

2. The optical detector device of claim 1, wherein the one or more processors are further to:
determine one or more other particulate sizes of one or more other particulates; and
determine one or more other identifications of the one or more other particulates; and
wherein the alert condition is determined to be satisfied further based on the one or more other particulate sizes and the one or more other identifications of the one or more other particulates.

3. The optical detector device of claim 1, wherein the one or more processors are further to:
transmit an instruction to cause a beam to be provided with the range of wavelengths; and
wherein the one or more processors, when receiving the spectroscopic measurement, are to:
receive the spectroscopic measurement as a response to transmitting the instruction.

4. The optical detector device of claim 1, wherein the one or more processors, when determining the identification of the particulate, are to:
determine, using a spectroscopic classification model, a classification of a spectrum of the particulate based on the spectroscopic measurement; and
determine the identification of the particulate based on the classification of the spectrum of the particulate.

5. The optical detector device of claim 1, wherein the one or more processors, when determining that the alert condition is satisfied, are to:
determine, based on determining that the particulate is the smoke-based particulate, that a fire is occurring within a proximity of the multispectral sensor.

6. The optical detector device of claim 5, wherein the one or more processors are further to:
determine, based on the spectroscopic measurement, a chemometric signature of the fire based on determining that the fire is occurring within the proximity of the multispectral sensor; and
wherein the one or more processors, when triggering the alert, are to:
provide information identifying the chemometric signature.

7. The optical detector device of claim 1, wherein the one or more processors, when triggering the alert, are to:
trigger an audible or visual alert to indicate the alert condition.

8. The optical detector device of claim 1, wherein the one or more processors, when triggering the alert, are to:
communicate with an emergency responder device to indicate the alert condition.

9. A fixed angle multispectral sensor device, comprising:
an optical transmitter to transmit a beam with a range of wavelengths;
a multispectral filter or lens to direct a reflection of the beam into a plurality of channels;
an optical receiver including a sensor element array to receive the reflection of the beam via the plurality of channels and to perform a spectroscopic measurement;
one or more processors to:
determine, based on the spectroscopic measurement, a particulate size of a particulate;
determine, based on the particulate size, that the particulate is a smoke-based particulate;
determine that an alert condition is satisfied based on the smoke-based particulate being a first type of smoke-based particulate that satisfies the alert condition, the first type of smoke-based particulate being different from a second type of smoke-based particulate that does not satisfy the alert condition; and
trigger a response action based on determining that the alert condition is satisfied.

10. The fixed angle multispectral sensor device of claim 9, wherein the range of wavelengths is from 190 nanometers (nm) to 1100 nm.

11. The fixed angle multispectral sensor device of claim 9, wherein the optical transmitter includes a first light emitter to transmit a first portion of the beam with a first portion of the range of wavelengths and a second light emitter to transmit a second portion of the beam with a second portion of the range of wavelengths.

12. The fixed angle multispectral sensor device of claim 9, wherein the sensor element array includes a first one or more sensor elements to receive a first portion of the reflection of the beam with a first portion of the range of wavelengths and a second one or more sensor elements to receive a second portion of the reflection of the beam with a second portion of the range of wavelengths.

13. The fixed angle multispectral sensor device of claim 9, wherein the optical transmitter is configured to transmit the beam, through a medium, toward particulates in the medium, and
wherein the medium is a gaseous medium or a liquid medium.

14. The fixed angle multispectral sensor device of claim 9, further comprising:
a housing with an opening,
a particulate inflow device to draw fluid from a first environment external to the housing to a second environment internal to the housing via the opening, wherein the optical transmitter is configured to transmit the beam and the optical receiver is configured to receive the reflection of the beam within the second environment internal to the housing.

15. The fixed angle multispectral sensor device of claim 9, wherein a sensitivity of the optical receiver is for particulates with a concentration of less than a threshold.

16. A method, comprising:
    receiving, by an optical detector device, a spectroscopic measurement from a multispectral sensor, wherein the spectroscopic measurement is performed at a fixed angle across a range of wavelengths;
    determining, by the optical detector device and based on the spectroscopic measurement, a particulate size of a particulate;
    determining, by the optical detector device and based on the spectroscopic measurement, an identification of the particulate;
    determining, by the optical detector device and based on the particulate size and the identification of the particulate, that the particulate is a smoke-based particulate;
    determining, by the optical detector device and that an alert condition is satisfied based on the smoke-based particulate being a first type of smoke-based particulate that satisfies the alert condition, the first type of smoke-based particulate being different from a second type of smoke-based particulate that does not satisfy the alert; and
    performing, by the optical detector device, an alert action to indicate the alert condition.

17. The method of claim 16, wherein performing the alert action comprises: providing an alert regarding a fire.

18. The method of claim 16, further comprising:
    transmitting an instruction to cause a beam to be provided with the range of wavelengths,
        wherein receiving the spectroscopic measurement comprises:
            receiving the spectroscopic measurement as a response to transmitting the instruction.

19. The method of claim 16, wherein determining the identification of the particulate comprises:
    determining, using a spectroscopic classification model, a classification of a spectrum of the particulate based on the spectroscopic measurement; and
    determining the identification of the particulate based on the classification of the spectrum of the particulate.

20. The method of claim 16, wherein determining that the alert condition is satisfied comprises:
    determining, based on determining that the particulate is the smoke-based particulate, that a fire is occurring within a proximity of the multispectral sensor.

* * * * *

UNITED STATES PATENT AND TRADEMARK OFFICE
CERTIFICATE OF CORRECTION

| | |
|---|---|
| PATENT NO. | : 11,137,331 B2 |
| APPLICATION NO. | : 16/530524 |
| DATED | : October 5, 2021 |
| INVENTOR(S) | : Houck |

Page 1 of 1

It is certified that error appears in the above-identified patent and that said Letters Patent is hereby corrected as shown below:

In the Claims

In Claim 16, Column 19, Line 26, "does not satisfy the alert;" should be changed to --does not satisfy the alert condition;--.

Signed and Sealed this
Twenty-third Day of November, 2021

Drew Hirshfeld
*Performing the Functions and Duties of the*
*Under Secretary of Commerce for Intellectual Property and*
*Director of the United States Patent and Trademark Office*